United States Patent [19]

Chaney

[11] Patent Number: 4,628,915
[45] Date of Patent: Dec. 16, 1986

[54] MALE ORGAN CONDITIONER ACCESSORY

[76] Inventor: John L. Chaney, 156 Broad St., Box 592, Lake Geneva, Wis. 53147

[21] Appl. No.: 734,074

[22] Filed: May 15, 1985

[51] Int. Cl.⁴ .............................................. A61F 5/00
[52] U.S. Cl. .................................. 128/79; 128/303 A
[58] Field of Search ............. 128/79, 325, 326, 303 A; 29/235

[56] References Cited

U.S. PATENT DOCUMENTS

| | | | |
|---|---|---|---|
| 823,877 | 6/1906 | Kellogg | 128/326 |
| 2,764,160 | 9/1956 | Alexander et al. | 128/326 |
| 3,382,873 | 5/1968 | Banich et al. | 29/235 |
| 3,726,278 | 4/1973 | Scott | 128/303 A |
| 3,760,810 | 9/1973 | Van Hoorn | 128/326 |
| 3,989,049 | 11/1976 | Yoon | 128/326 |
| 4,257,419 | 3/1981 | Göltner et al. | 128/326 |
| 4,291,451 | 4/1981 | O'Neill et al. | 29/235 |
| 4,493,319 | 1/1985 | Polk et al. | 128/326 |
| 4,548,201 | 10/1985 | Yoon | 128/326 |
| 4,553,300 | 11/1985 | Mancha | 29/235 |

Primary Examiner—Robert Peshock
Assistant Examiner—Cary E. Stone
Attorney, Agent, or Firm—Fuller, House & Hohenfeldt

[57] ABSTRACT

A cone and an integral cylinder projecting coaxially from the base of the cone. A sleeve is slidable onto the cylinder and detents latch the sleeve on the cylinder. An elastic ring which is for contracting on the penis to maintain an erection, is expanded by sliding it over the cone until it slips onto the sleeve. The sleeve is unlatched by twisting it to depress the detents and is slipped off of the cylinder with the elastic ring on it. The sleeve with the ring on it is slipped to the base of the penis and the ring to slid off for contracting.

7 Claims, 8 Drawing Figures

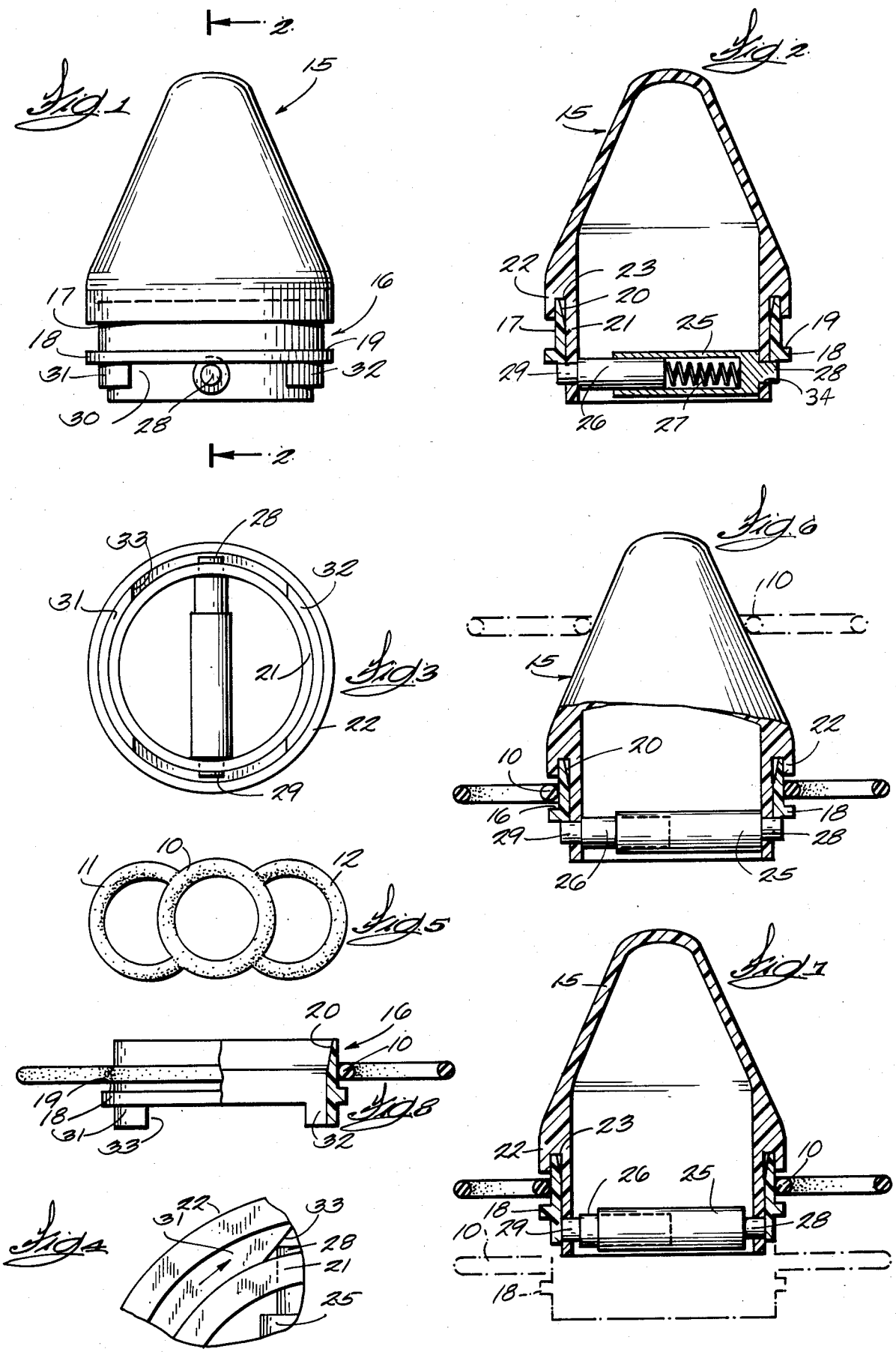

MALE ORGAN CONDITIONER ACCESSORY

BACKGROUND OF THE INVENTION

This invention pertains to an accessory that facilitates use of a Male Organ Conditioner device which is described in U.S. patent application Ser. No. 530,523, filed Sept. 9, 1983, now U.S. Pat. No. 4,539,980, dated Sept. 10, 1985.

The plan view of the Male Organ Conditioner device described in the cited patent is depicted in FIG. 5 of this application. The device in FIG. 5 comprises a central elastic, preferably latex, ring 10 which has a circular cross section and has two finger gripping loops 11 and 12 molded integrally with the central ring. The elements 11 and 12 are engaged by the users fingers to stretch out the ring in four directions, preferably so it will fit over the penis of a male. When the gripping elements 11 and 12 are released, the central ring contracts onto the base or root of the penis such as to prevent outflow of veinous blood from the penis and yet permit blood to be manually massaged into the penis. The device is for creating and maintaining an erect penis so that pleasurable sexual intercourse can be accomplished. In contemplation of intercourse after the device has been deposited on the penis, the male user presses his hand in the groin or crotch area and massages blood forwardly into the penis against the elastic pressure created by ring 10. When a massage stroke is terminated, the elastic ring acts to prevent outflow. After several massage strokes, enough blood will be forced into the penis and enough pressure will be developed to produce a lasting erection.

Applying the elastic ring to the penis requires a little bit of deftness to stretch the central ring quadrilaterally so it clears the outside of the penis as it is being applied. This is not as convenient as it could be and it takes time when some might consider that time is of the essence. Obviously a device that keeps the user prepared to apply the ring quickly and easily can be highly advantageous and that is the objective of the present invention.

SUMMARY OF THE INVENTION

The invention is an accessory that is comprised of a cone that can be coupled to a cylindrical carrier sleeve. The elastic central ring of the organ conditioner device is manually forced over the cone to expand it and let it be transferred to the carrier sleeve. The sleeve is then uncoupled from the cone and slipped over the penis to the base. Then the elastic ring 10 is slipped off of the accessory sleeve to thereby put the organ conditioner device in the proper position on the penis.

How the accessory is constructed and used will now be described in detail in reference to the accompanying drawing.

DESCRIPTION OF THE DRAWING

FIG. 1 is a side elevation view of the new accessory;

FIG. 2 is a vertical section taken on a line corresponding with 2—2 in FIG. 1;

FIG. 3 is an end or bottom view of the accessory;

FIG. 4 is an enlarged fragment of the device for explaining how the plastic carrier sleeve on which the elastic male organ conditioner ring is deposited is separated from the cone;

FIG. 5 is a plan view of the male organ conditioner device;

FIG. 6 is a vertical section similar to FIG. 2 except that the male organ conditioner device is installed on the accessory;

FIG. 7 is similar to FIG. 6 but shows how the sleeve on which the accessory is deposited is detached from the cone, the sleeve with the ring on it being shown in phantom lines; and, FIG. 8 depicts the organ conditioner device deposited on a sleeve which has been detached from the cone.

DESCRIPTION OF A PREFERRED EMBODIMENT

FIG. 1 shows the accessory as being comprised of two separable parts, a cone 15 and an organ conditioner carrier and applicator sleeve 16. These parts are preferably molded of a rigid plastic material. The carrier sleeve 16 comprises a cylindrical portion 17 which has an integral annular rib 18 that provides an annular shoulder 19. As can be seen in FIG. 2, the interior edge of the cylindrical portion 17 of carrier sleeve 16 is beveled radially outwardly as indicated where the reference numeral 20 is applied. The bevel facilitates slipping sleeve 16 over the end of a cylindrical portion 21 extending coaxially from the base of cone 15. The cone has an annular shoulder 22 which has an annular groove 23. The cylindrical end of sleeve 16 makes a relatively loose fit in groove 23. As is evident in FIG. 2, means are provided for temporarily latching sleeve 17 on the cylindrical portion 21 of the cone 15. The latch means constitutes a detent assembly which, as can be seen in FIG. 2, is similar to the well known telescoping toilet paper holder spindle in that it comprises a hollow cylinder 25 in which there is a plunger 26 which is biased in an axial direction by a compression spring 27. The cylinder 25 and plunger 26 have reduced diameter axially extending detent pins 28 and 29 integral with them. These detent pins project through diametrically opposite holes 34 in cylindrical part 21 at the base of the cone 15. An axial force on plunger 26 causes its detent 27 to retract in hole 34 sufficiently to allow the plastic carrier sleeve 16 to be slipped off of cylindrical part 21 of the cone 15. The detent assembly will remain in place because the detents are always forced outwardly by the spring 27 and the detents only need to retract until their outer ends are flush with the outside of the cylinder 21 to let the sleeve 16 slide off.

Considering FIG. 1 in conjunction with FIG. 3, one may see that the lower edge of the carrier sleeve is cut away, that is, there is a wide transverse slot 30 cut across the carrier sleeve to thereby let two arcuate wall sections 31 and 32 remain. Each wall section thus has a beveled edged such as the one marked 33. FIG. 4 illustrates how when the section 31 of sleeve 16 is rotated on cone base 21, the beveled edge 33 reaches the detent 28, for example, and wedges it and causes it to plunge back into the wall of cylindrical cone extension 21 so that the sleeve can be slid off of the cone. FIG. 1 shows how, before the sleeve is rotated, the detent pin 28 which is driven outwardly by spring 27 lies under the rib 18 to thereby hold the carrier sleeve on the cylindrical part 21 of the cone.

FIG. 6 is for demonstrating how the organ conditioner ring 10 of FIG. 5 is pushed over cone 15 to expand the ring 10 as indicated in phantom lines until its diameter is increased to the diameter of the cone base whereupon it can be slipped off of the cone and onto the carrier sleeve 16 which is shown in section in FIG. 6. It is desirable to have adequate clearance in the axial direction between the shoulder 22 on the cone and and the shoulder of rib 18 on the carrier sleeve 16. If there is not adequate clearance to prevent the high friction latex central ring 10 of the conditioner device from rubbing against the lower edge of the cone, rotation of sleeve 16 to unlatch it for being slid off of the cone can be very difficult. It is desirable to wet the latex to make it slip more easily over the cone and avoid rolling and twisting action by the central ring 10 when deposited on carrier sleeve 16. The carrier sleeve is ready for removal with the latex sleeve on it as indicated by the phantom depiction of carrier sleeve 16 in FIG. 7.

FIG. 8 shows the carrier sleeve 16 separated from the cone 15. As mentioned earlier, the carrier as depicted in FIG. 8 with the elastic ring on it is now ready for being slipped over the male penis to its base so the elastic ring can be slipped off of the carrier sleeve to contract onto the penis. Massaging of blood into the penis is then undertaken and the latex ring prevents the blood flowing back into the circulatory system for the duration of the erection.

The separable sleeve 16 provides a great convenience in that after the elastic ring 10 is deposited on it, it may put in a man's pocket and carried to a site where sexual intercourse is contemplated and it will be ready for retreival and application of the elastic ring when the time for sexual intercourse arrives.

I claim:

1. A device for disposing an elastic ring in a stretched condition on a cylindrical rigid sleeve so that the sleeve may be slipped over the penis and the ring slid off of the sleeve to contract on the penis and control blood flow to the penis for facilitating obtaining and maintaining penile erection, comprising:
    a member having a conical part and a generally circular base part from which said conical part extends and a cylindrical part joined coaxially with said circular base part, said cylindrical part having an outside diameter smaller than the outside diameter of said base part such that an annular shoulder is defined on said conical part where said conical part joins said cylindrical part, said shoulder having an annular groove concentric to said cylindrical part,
    a cylindrical rigid sleeve slidable onto said cylindrical part of said member, said sleeve having axially opposite ends one of which extends into said annular groove in said shoulder, and
    releasable retaining means for retaining said sleeve on said cylindrical part to facilitate sliding said elastic ring over said conical part of said member and onto said sleeve,
    release of said retaining means enabling said sleeve to be separated from said cylindrical part of said member with said elastic ring on it.

2. A device for disposing an elastic ring in a stretched condition on a cylindrical rigid sleeve so that the sleeve may be slipped over the penis and the ring slid off of the sleeve to contract on the penis and control blood flow to the penis for facilitating obtaining and maintaining penile erection, comprising:
    a member having a conical part and a generally circular base part from which said conical part extends and a cylindrical part joined coaxially with said circular base part, said cylindrical part having an outside diameter smaller than the outside diameter of said base part such that an annular shoulder is defined on said base part where said base part joins said cylindrical part, said shoulder having an annular groove concentric to said cylindrical part,
    a cylindrical rigid sleeve slidable onto said cylindrical part of said member, said sleeve having axially opposite ends one of which extends into said annular groove in said shoulder,
    an annular rib on said cylindrical sleeve, said rib being spaced from said shoulder by substantially more than the thickness of said elastic ring when said sleeve is retained on said cylindrical part of said member, and
    releasable retaining means for retaining said sleeve on said cylindrical part to facilitate sliding said elastic ring over said conical part of said member and onto said sleeve,
    release of said retaining means enabling said sleeve to be separated from said cylindrical part of said member with said elastic ring on it.

3. A device for disposing an elastic ring in a stretched condition on a cylindrical rigid sleeve so that the sleeve may be slipped over the penis and the ring slid off of the sleeve to contract on the penis and control blood flow to the penis for facilitating obtaining and maintaining penile erection, comprising:
    a member having a control part and a generally circular base part from which said conical part extends and a cylindrical part joined coaxially with said circular base part, said cylindrical part having an outside diameter smaller than the outside diameter of said base part such that an annular shoulder is defined on said base part where said base part joins said cylindrical part, said shoulder having an annular groove concentric to said cylindrical part,
    latch means including a tubular part having a detent pin at one end, a plunger slidable coaxially in said tubular part and having a detent pin at an end outside of the tubular part, a spring in said tubular part for urging said plunger axially outwardly of said tubular part, said cylindrical part of said member having diametrically opposite holes through which said detent pins extends, respectively,
    a cylindrical rigid sleeve slidable onto said cylindrical part of said member, said sleeve having axially opposite ends one of which extends into said annular groove in said shoulder, sliding of said sleeve onto said cylindrical part depressing said detent pins diametrically inward toward each other until said sleeve has passed whereupon said spring biases said detent pin diametrically outward to thereby retain said sleeve on said member so that said elastic ring can be slid over said conical part onto said sleeve and said detent pins can be depressed in opposition to said spring to let said sleeve slide off of said cylindrical part with said elastic ring on it.

4. The device according to claim 3 wherein said one end of said sleeve is beveled internally to facilitate depressing said detent pins while said sleeve is being slid onto said cylindrical part.

5. The device according to any one of claims 3 or 4 wherein the other end opposite of said one end of said sleeve has diametrically opposite notches each defined by two circumferentially spaced apart axially extending edges and a circumferentially extending edge, sliding said sleeve onto said cylindrical part sufficiently for said circumferentially extending edges to pass said detent pins allowing said pins to be urged diametrically outward to thereby retain said sleeve on said cylindrical part.

6. The device according to claim 5 wherein said axially extending edges are beveled so that by twisting said sleeve said edges will slide over said detent pins and depress said pins to allow said sleeve to be slid off of said cylindrical part.

7. The device according to claim 5 wherein said sleeve has an annular rib extending radially outwardly of the external periphery of said sleeve and adjacent said circumferentially extending edge of said notch.

* * * * *